United States Patent
Manning et al.

(10) Patent No.: US 9,861,909 B2
(45) Date of Patent: Jan. 9, 2018

(54) SOLID PHASE MICRO-EXTRACTION (SPME) DEVICES

(71) Applicant: SMITHS DETECTION INC., Danbury, CT (US)

(72) Inventors: David D. Manning, Keeseville, NY (US); Kenneth C. Schreiber, Sandy Hook, CT (US); Kenneth J. Fredeen, Monroe, CT (US); George E. Riehm, New Fairfield, CT (US); Greg Weaver, Waterbury, CT (US); John R. Laverack, Southbury, CT (US)

(73) Assignee: Smiths Detections Inc., Danbury, CT (US)

( * ) Notice: Subject to any disclaimer, the term of this patent is extended or adjusted under 35 U.S.C. 154(b) by 16 days.

(21) Appl. No.: 14/357,985

(22) PCT Filed: Nov. 14, 2012

(86) PCT No.: PCT/US2012/065056
§ 371 (c)(1),
(2) Date: May 13, 2014

(87) PCT Pub. No.: WO2013/074657
PCT Pub. Date: May 23, 2013

(65) Prior Publication Data
US 2014/0311985 A1 Oct. 23, 2014

Related U.S. Application Data

(60) Provisional application No. 61/559,354, filed on Nov. 14, 2011, provisional application No. 61/648,367, filed on May 17, 2012.

(51) Int. Cl.
*G01N 30/04* (2006.01)
*G01N 30/16* (2006.01)
(Continued)

(52) U.S. Cl.
CPC ............ *B01D 15/00* (2013.01); *G01N 1/405* (2013.01); *G01N 2030/009* (2013.01); *G01N 2030/062* (2013.01); *G01N 2035/1053* (2013.01)

(58) Field of Classification Search
CPC .. B01D 15/00; G01N 1/405; G01N 2030/009; G01N 2030/062; G01N 2035/1053
See application file for complete search history.

(56) References Cited

U.S. PATENT DOCUMENTS

| 3,819,282 A | 6/1974 | Schultz |
| 5,691,206 A | 11/1997 | Pawliszyn |

(Continued)

FOREIGN PATENT DOCUMENTS

| EP | 1767623 | 3/2007 |
| WO | 91/15745 | 10/1991 |

(Continued)

OTHER PUBLICATIONS

European Supplemental Search Report for EP12849535.5, dated Jul. 13, 2015, 7 pages.

(Continued)

*Primary Examiner* — Robert Eom
(74) *Attorney, Agent, or Firm* — Casimir Jones SC; David W. Staple

(57) ABSTRACT

Provided herein are improved solid phase micro-extraction (SPME) devices, systems comprising such devices, and methods of use and manufacture thereof. In particular, SPME devices provided herein are configured to prevent damage (e.g., to the device and/or to a system in which they are employed) incurred, for example, through user error.

8 Claims, 21 Drawing Sheets

(51) Int. Cl.
*G01N 1/10* (2006.01)
*B01D 15/00* (2006.01)
*G01N 1/40* (2006.01)
G01N 30/00 (2006.01)
G01N 30/06 (2006.01)
G01N 35/10 (2006.01)

(56) References Cited

U.S. PATENT DOCUMENTS

| | | |
|---|---|---|
| 6,164,144 A | 12/2000 | Berg |
| 6,405,608 B1 | 6/2002 | Lindgren et al. |
| 6,759,126 B1 | 7/2004 | Malik et al. |
| 2002/0150513 A1 | 10/2002 | Nunes et al. |
| 2003/0003596 A1 | 1/2003 | Pawliszyn |
| 2006/0123931 A1 | 6/2006 | Wareham et al. |
| 2006/0241515 A1* | 10/2006 | Jones .................... A61B 10/02 600/562 |
| 2009/0260456 A1* | 10/2009 | Degli Esposti ........ G01N 1/405 73/863.21 |
| 2010/0247378 A1* | 9/2010 | Cerra ................. G01N 35/1011 422/67 |

FOREIGN PATENT DOCUMENTS

| | | |
|---|---|---|
| WO | 98/41855 | 9/1998 |
| WO | 2013/074657 | 5/2013 |

OTHER PUBLICATIONS

International Search Report and Written Opinion for PCT/US2012/065056, dated Feb. 5, 2013, 8 pages.

\* cited by examiner

A  B

A

B

C

SOLID PHASE MICRO-EXTRACTION (SPME) DEVICES

CROSS-REFERENCE TO RELATED APPLICATIONS

The present invention claims the benefit of the U.S. Provisional Patent Application No. 61/559,354, filed Nov. 14, 2011, and U.S. Provisional Patent Application No. 61/648,367, filed May 17, 2012, each of which is incorporated by reference in their entireties.

FIELD

Provided herein are improved solid phase micro-extraction (SPME) devices, systems comprising such devices, and methods of use and manufacture thereof. In particular, SPME devices provided herein are configured to prevent damage (e.g., to the device and/or to a system in which they are employed) incurred, for example, through user error.

BACKGROUND

Solid phase micro-extraction (SPME) was developed by Janusz Pawliszyn of the University of Waterloo, Ontario, Canada. The SPME process and apparatus is disclosed for example in International Patent (PCT) Publication WO 91/15745 of J. Pawliszyn, published Oct. 17, 1991, and incorporated herein by reference in its entirety.

In the SPME process, a coated or uncoated fiber (filament) housed within a needle of a syringe is brought into contact with components/analytes in a fluid carrier or headspace above the carrier for a sufficient period of time for extraction of the analytes to occur onto the fiber or coated fiber. Subsequently the fiber is removed from the carrier or headspace above the carrier and the analytes desorbed from the fiber generally by thermal desorption into an analytical instrument, such as a gas chromatograph (GC), for detection and quantification of the analytes.

SUMMARY

In embodiments, provided herein are solid phase micro-extraction (SPME) devices comprising a filament and a component to prevent disengagement of the SPME device from an instrument to which it is engaged when the filament is extended. The component comprises a filament extension/retraction mechanism that automatically retracts the filament from the instrument in the absence of downward pressure placed upon the SPME device by a user. The component may comprises an indicator signal that provides a visual and/or audible cue indicating to a user that the filament is extended. The component can comprise an interference mechanism that prevents a filament from remaining extended in the absence of downward pressure placed upon the SPME device by a user when the SPME device is engaged with the instrument. In some embodiments, the component comprises a locking mechanism that prevents disengagement of the SPME device from the instrument when the filament is extended. The locking mechanism, in some embodiments, extends from the SPME device to engage with the instrument when the filament is extended. In some embodiments, the locking mechanism withdraws into the SPME device to allow disengagement and/or engagement of the locking mechanism with the instrument when the filament is retracted.

Methods are described that can reduce the risk of breaking a solid phase micro-extraction (SPME) filament comprising preventing an SPME device from being disengaged from an associated instrument while the SPME filament is extended. In some embodiments, preventing comprises physically preventing disengagement of the SPME device from the associated instrument while the filament is extended. In some embodiments, preventing comprises alerting a user to the fact that the filament is extended. In some embodiments, preventing comprises coupling the action of disengagement of the SPME device from the associated instrument to retraction of the filament.

In some embodiments, provided herein are solid phase micro-extraction (SPME) devices comprising a filament and a locking mechanism, wherein the locking mechanism prevents the SPME device from being removed from an instrument to which it is engaged when the filament is in an extended conformation. In some embodiments, the SPME device is locked to the instrument when the locking mechanism is activated. In some embodiments, the locking mechanism is automatically activated upon extension of the filament. In some embodiments, the locking mechanism is automatically deactivated upon retraction of the filament.

DETAILED DESCRIPTION

Figure 1:
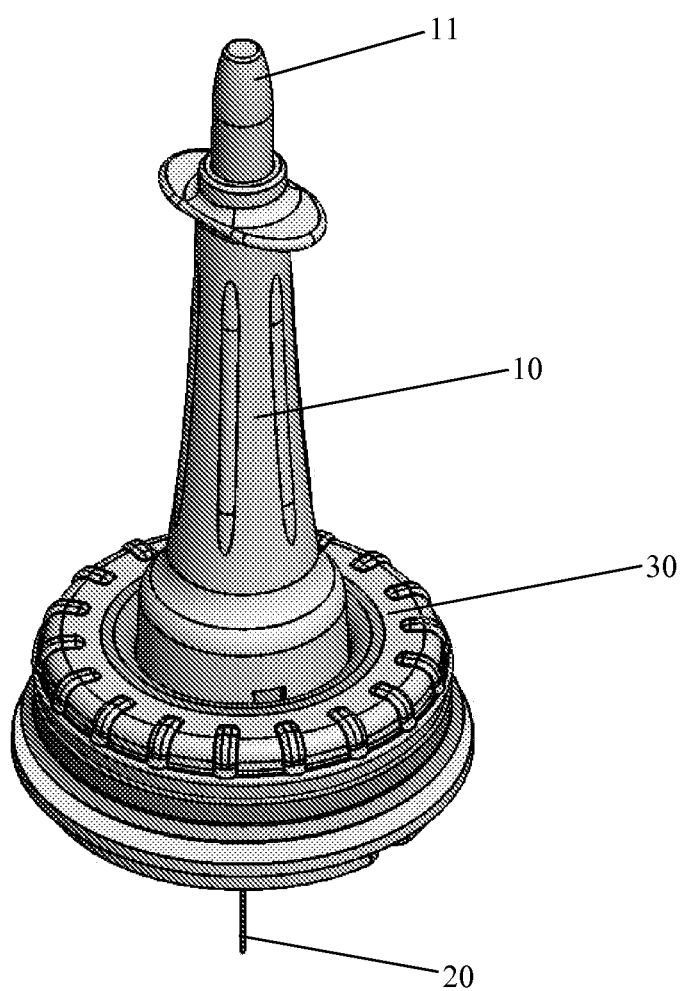
FIG. 1 is an exterior view of an embodiment of a SPME device.

Provided herein are improved solid phase micro-extraction (SPME) devices, systems comprising such devices, and method of use and manufacture thereof. In particular, SPME devices provided herein are configured to minimize the likelihood or prevent damage (e.g., to the device and/or to a system in which they are employed) incurred, for example, through user error. In embodiments, SPME devices are provided that prevent disengagement/removal of the device from an instrument when the filament is extended from the device into the instrument. By reducing the likelihood of and/or preventing disengagement of a SPME device from an instrument while the filament is extended, the mechanisms described herein, and the SPME devices incorporating them, reduce the likelihood of and/or prevent breakage of the filament within the instrument and the various consequences associated therewith (e.g., damage to SPME, replacement of filament, replacement of SPME device, contamination of instrument, damage to instrument, downtime, sample loss, etc.).

SPMEs can be configured so the fiber cannot be left exposed (e.g., accidentally, due to operator error, etc.) when removing the SPME from an instrument, such as an analytical instrument such as a mass spectrometer, gas chromatograph, infrared spectrometer and the like. Embodiments, described herein prevent and/or reduce the likelihood of SPME filament breakage within an instrument by one or more of: altered extension/withdrawal mechanism (SEE FIG. 2), extension/withdrawal interference mechanism (SEE FIGS. 3-4), extended filament indicators (e.g., SEE FIGS. 5 thru 9), filament locks (e.g., FIGS. 8-9), and device locks (SEE FIGS. 10-15). The SPME devices and methods can avoid device disengagement while the filament is extended by any suitable component/means/mechanisms. Filament extension/withdrawal mechanisms are described that force a user to physically interact with the device (e.g., apply pressure to the device housing, apply pressure to a button, etc.) for the filament to adopt the extended conformation (SEE FIG. 2). Interference mechanisms are also described that prevent the filament from remaining in the extended conformation, without affirmative interaction (e.g., downward pressure) by a user, when the device is engaged with an instrument (SEE FIGS. 3-4). One or more indicators (e.g., lights (e.g., LEDs), mechanical flags, etc.) can be provided that draw a user's attention to the fact that the filament is extended (e.g., within the instrument) (SEE FIGS. 5 thru 9). Filament locks are also described to hold a filament in an extended conformation, but cannot adopt the locked conformation when the SPME device is engaged with an instrument (SEE FIGS. 8-9). Locking devices and mechanisms can be provided that only allow the SPME device to disengage from an instrument once the fiber is drawn into the SPME (SEE FIGS. 10-15). It is to be apparent that various combinations of the described structures, devices, approaches (including method of use and of manufacture) may be implemented in various implementations, it is the intention of this document to include such variation.

Example SPME devices are described in, for example: U.S. Pat. Pub. No. 2006/0241515; U.S. Pat. No. 5,691,206; U.S. Pat. No. 6,164,144; U.S. Pat. No. 6,405,608; and U.S. Pat. No. 6,759,126; each of which is herein incorporated by reference in their entireties.

In embodiments, an SPME device comprises a filament extension/retraction mechanism that prevents and/or reduces the likelihood of the filament being extended when the SPME device is removed/withdrawn/disengaged from an instrument. In embodiments, a filament extension/retraction mechanism requires that a user take an affirmative step (e.g., applying pressure to a button, applying pressure to the housing, etc.) in order for the filament to be in an extended position (and therefore within the instrument). In embodiments, a filament extension/retraction mechanism requires a constant affirmative step (e.g., applying pressure to a button, applying pressure to the housing, etc.) in order for the filament to be in an extended position (and therefore within the instrument). In the absence of user intervention, such as an affirmative action by the user, the filament cab be withdrawn/retracted into the SPME and out of the instrument. The filament can automatically withdraw into the SPME device (and out of the instrument) in the absence of downward pressure on the device, device housing, and/or a bottom or other portion of the device. Extension of the filament from the SPME device can require a user's hand to be in contact with the SPME device.

Extension/retraction mechanisms requiring a constant affirmative action for extension of the filament prevent or reduce the likelihood of filament breakage because the action required for filament extension is not compatible (or less compatible) with disengagement with the instrument. In embodiments, a user ceases the affirmative extension action in order to perform a device disengagement action. In other embodiments, performing the device disengagement action (e.g., lifting up of device) is in direct opposition to the filament extension action (e.g., downward pressure on device).

A retraction/extension mechanism may: (1) function identically whether a device is engaged or disengaged with an instrument, or (2) operate in different extension/retraction modes when engaged and disengaged from an instrument. In some embodiments, when engaged with an instrument, extension of the filament from an SPME device and into an instrument requires actuation, such as pressure (e.g., downward pressure) from a user, or some other affirmative action. Release of an affirmative action can results in retraction of the filament including, but not limited to, withdrawal from the instrument and drawing the filament into a sheath or body of the SPME. In certain embodiments, the same action is required for extension of the filament when the SPME device is not engaged with an instrument. However, in other embodiments, when the device is not engaged with an instrument, the filament is configured to remain extended without constant affirmative action by a user. In some embodiments, when a device is not engaged with an instrument, the filament extension/retraction mechanism functions similarly to a retractable pen, either in the actual mechanism for retraction/extension or in the end result (e.g., a first press/release extends the filament, a second press/release retracts the filament). By switching the device to a press/release filament-extension mode when a device is not engaged with an instrument, the ease of sample loading and/or filament cleaning is enhanced, while preventing filament breakage within the instrument.

One or more suitable mechanisms can be provided to switch the SPME device from an engaged retraction/extension mode (e.g., constant affirmative action to remain extended) to a disengaged retraction/extension mode (e.g., press and release retraction/extension). In embodiments, an interference element (e.g., coil, sleeve, rod, foot, etc.) is provided that interferes with the press and release mechanism to force the device into a mode that implements affirmative action for extension of the filament (See FIGS. 3-4). In some embodiments, any suitable means or mechanism for switching a device from a press/release mode to constant pressure mode finds use in embodiments described herein.

In some embodiments, a SPME device comprises one or more indicators (e.g., indicator light (e.g., LED), mechanical flag, audible indicator, etc.) that alerts a user that the filament is extended (e.g., within an instrument). Such indicators serve to prevent disengagement of a SPME device from an instrument when the filament is extended by alerting/reminding a user that the filament is extended. In embodiments, an indicator is activated whenever the filament is extended. In other embodiments, an indicator is only activated when the filament is extended and the device is engaged with an instrument. A device may comprise one or more (e.g., 1, 2, 3, 4, 5, 6, or more) indicators of any type (e.g., visual (e.g., light, LED, flag, etc.) or audible (e.g., alarm)) located at any suitable location on the SPME device (e.g., top, base, shaft, exterior, interior, etc.).

In embodiments, SPME devices are provided that require constant affirmative action to extend the filament, but also comprise a locking means that when engaged allows a user to cease applying the pressure without retraction of the filament. The locking means allows a user to lock the filament in the extended position when the device is not engaged with an instrument (SEE FIGS. 8-9). This enables a user to more easily clean a filament and/or load a sample. However, in particular embodiments, engagement of the locking means (e.g., locking the extended filament) is physically incompatible with device-engagement with an instrument. In other words, the filament can be locked in an extended position, only when the device is not engaged with an instrument. Such a locking mechanism allows for ease of filament cleaning and/or loading while still allowing a constant affirmative action extension/retraction mechanism to reduce the likelihood of device withdrawal when the filament is extended. Suitable locking means and/or mechanisms may be located at any suitable position on the device (e.g., base, bottom, etc.) and may be engaged/activated by any suitable user action (e.g., slide, press, twist, turn, etc.). In some embodiments, activation of the locking mechanism results in a protrusion from the SPME device that is physically incompatible with engagement of the device with the instrument. In some embodiments, engagement of the device with the instrument results in a fit between the device and instrument that is physically incompatible with locking of the filament.

In certain embodiments, an SPME device comprises a locking mechanism that prevents the device from being disengaged from an instrument when the filament is extended. In some embodiments, upon extension of the filament, a locking element (e.g., at the base of the device) engages with the instrument to prevent disengagement of the device and instrument. In some embodiments, only once the filament has been withdrawn can the device and instrument be disengaged. In some embodiments, a device lock functions through any suitable means and/or mechanisms (See, e.g., FIGS. 10-15). In some embodiments, a device lock allows a filament to be extended/retracted by any mechanism (e.g., constant pressure, press and release, etc.) without risk of the device being withdrawn from the instrument while the filament is extended. Without withdrawing the filament, the device cannot be disengaged from the instrument.

In certain embodiments, an instrument comprises a port for proper engagement with a device described herein. In some embodiments, an instrument port in modified for proper interaction with an SPME device or a portion thereof (e.g., locking means/mechanism).

Any useful combination of the filament-breakage prevention means and mechanisms described herein (e.g., extension/retraction mechanisms, interference mechanisms, indicators, filament locks, device locks) find use in embodiments described herein.

In certain embodiments, the SPME devices of the present invention will not require the operator to keep their hand on the SPME to keep the fiber in the exposed position both in and out of the test device. In some embodiments, the act of exposing and retracting the SPME fiber will be capable of being accomplished with a one handed operation (e.g., while the user is in a level A Hazmat suit). In particular embodiments, the SPME devices incorporate feedback indicating proper seating of the SPME or a design that ensures proper seating by design. In particular embodiments, the fiber of the SPME has the capability of being exposed both in open air to gather a sample, as well as in the test device (e.g., FiRMS instrument). In particular embodiments, the SPME device has the capability to initiate a test device (e.g., GC/MS) run by contacting the pogo pins in a universal sampler interface.

In many conventional SPME devices, a button, typically located at the top of the device, provides a means for extending and retracting the filament. When the filament is in the retracted position, the button is depressed and released, thereby extending the filament. When the filament is in the extended position, the button is depressed and released (in identical fashion to the extension process), thereby retracting the filament. The extension and retraction of the filament from many conventional SPME devices functions similarly to the internal mechanism of a retractable pen (See, e.g., U.S. Pat. No. 3,819,282). Some embodiments described herein utilize such a press and release extension/retraction mechanism. In some of such embodiments, a stepper mechanism allows the pressing and releasing of a single button to extent the filament, and the same press and release motion to retract the filament. This configuration has the advantages of allowing the filament to remain extended (e.g., for sample loading when not engaged with an instrument, for sample testing when engaged with an instrument, etc.) without a user having to take a prolonged affirmative action (e.g., holding the button down). However, when using such an SPME device, an affirmative step must be taken to retract the filament (e.g., depressing the button), before disengaging the SPME from the instrument. As addressed above, if the SPME is withdrawn while the filament is inserted into the instrument, the filament can become stuck in the instrument, causing damage to both the SPME and the instrument, loss of sample, and contamination of the instrument. FIGS. 2-15 demonstrate various embodiments of SPME configurations that can be used to avoid the problems with breakage of the filament.

Figure 2:
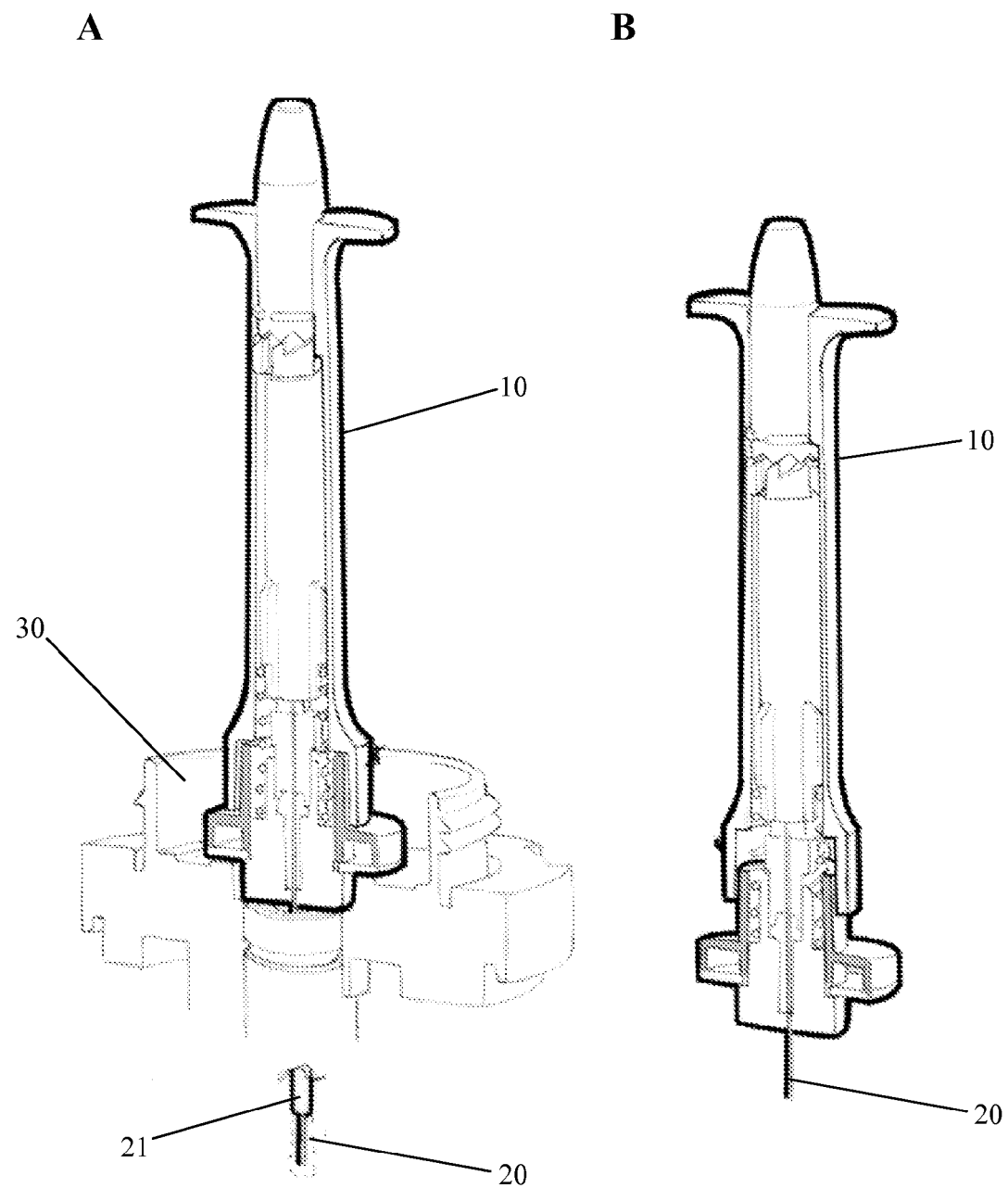
FIG. 2 is an interior view of an embodiment of a SPME device in which the entire housing is depressed to reveal the filament; A) SPME engaged with instrument, housing depressed, and filament extended; B) SPME disengaged from instrument.

FIG. 2 demonstrates an embodiment of an SPME device in which a downward force (e.g., from a user's hand) on the housing 10 extends the filament 20 from the SPME, rather than depressing/releasing the button. The filament 20 remains in the extended configuration as long as sufficient downward pressure is applied to the device housing 10. When pressure is released, the filament is withdrawn into the SPME. This configuration has the advantage of automatically protecting the filament 20 upon disengagement from an instrument 30. In order to load a sample into/onto the filament 20, the housing 10 must also be pushed down, and held in the depressed conformation for the duration of the loading.

Figure 3:
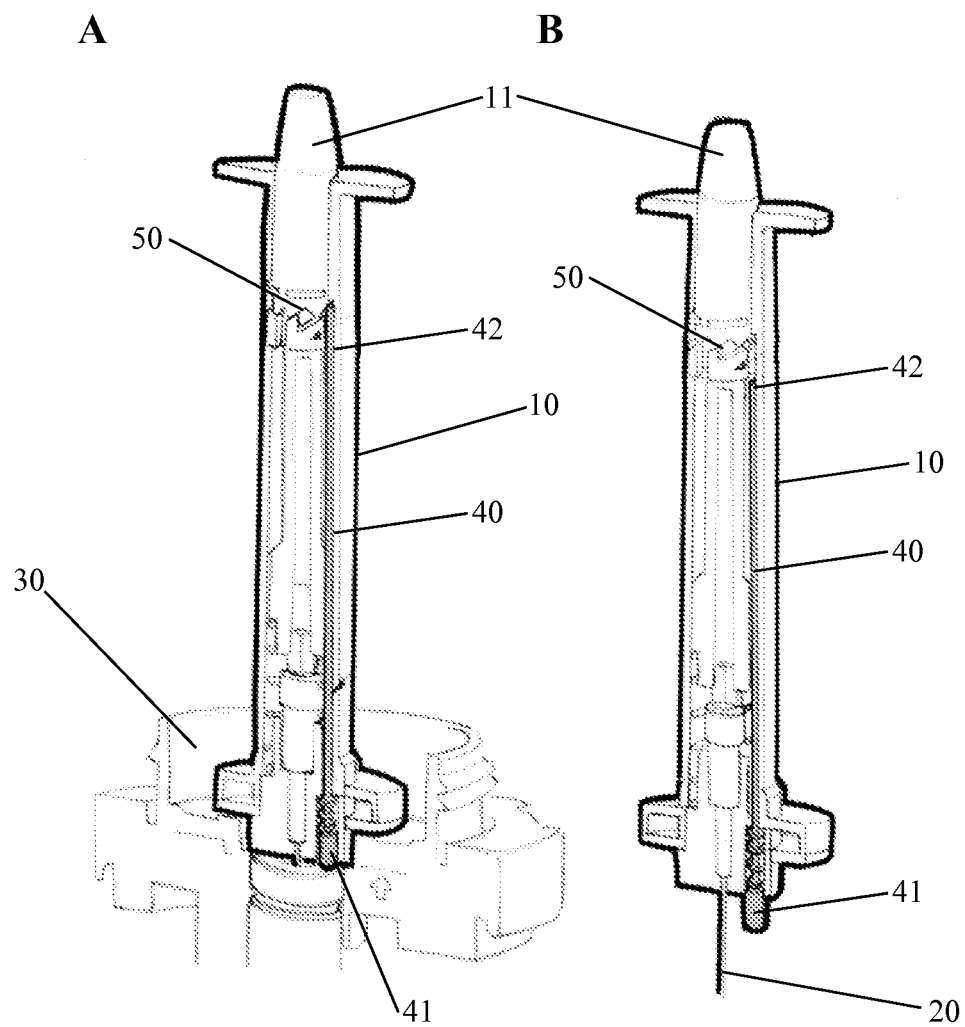
FIG. 3 is a cut-away view of an embodiment of a SPME device in which an interference rod prevents the filament from being locked in the extended position when the SPME is engaged with an instrument; A) SPME engaged with instrument and interference rod depressed; B) disengaged SPME and interference rod extended.

FIG. 3 demonstrates an embodiment of an SPME device in which functions via the conventional button 11 mechanism, but also includes an interference rod 40 that prevents the filament 20 from being locked in the extended position when the SPME is engaged with an instrument 30. When the SPME is disengaged from an instrument 30 (FIG. 3B), the interference rod 40 sits in an extended conformation in which the lower end 41 of the interference rod 40 extends beneath the base of the SPME and the upper end 42 of the interference rod 40 does not interfere with the stepper mechanism 50. In such a configuration, the button 11 is depressed/released to extend the filament 20 (e.g., for cleaning, for sample loading, etc.) and depressed/released to retract the filament 20 (e.g., to prepare for engagement of the SPME with the instrument 30). However, when the SPME engages with the instrument 30 (FIG. 3A), the interference rod 40 is depressed so the lower end 41 is flush with the base of the SPME and the upper end 42 of the interference rod 40 engages (e.g., interferes) with the stepper mechanism 50. In such a configuration, depressing the button 11 extends the filament 20 (e.g., for sample testing, etc.), but release of the button 11 results in the filament 20 being withdrawn into the SPME. If the user is not actively depressing the button 11, the filament 20 is withdrawn into the SPME. In such an embodiment, the button 11 is depressed for the duration of the testing. The user need only cease applying pressure to the button 11, prior to disengaging the SPME with the instrument 30, to prevent the filament 20 being in the extended conformation during the disengagement (e.g., resulting in damage to the filament 20).

Figure 4:
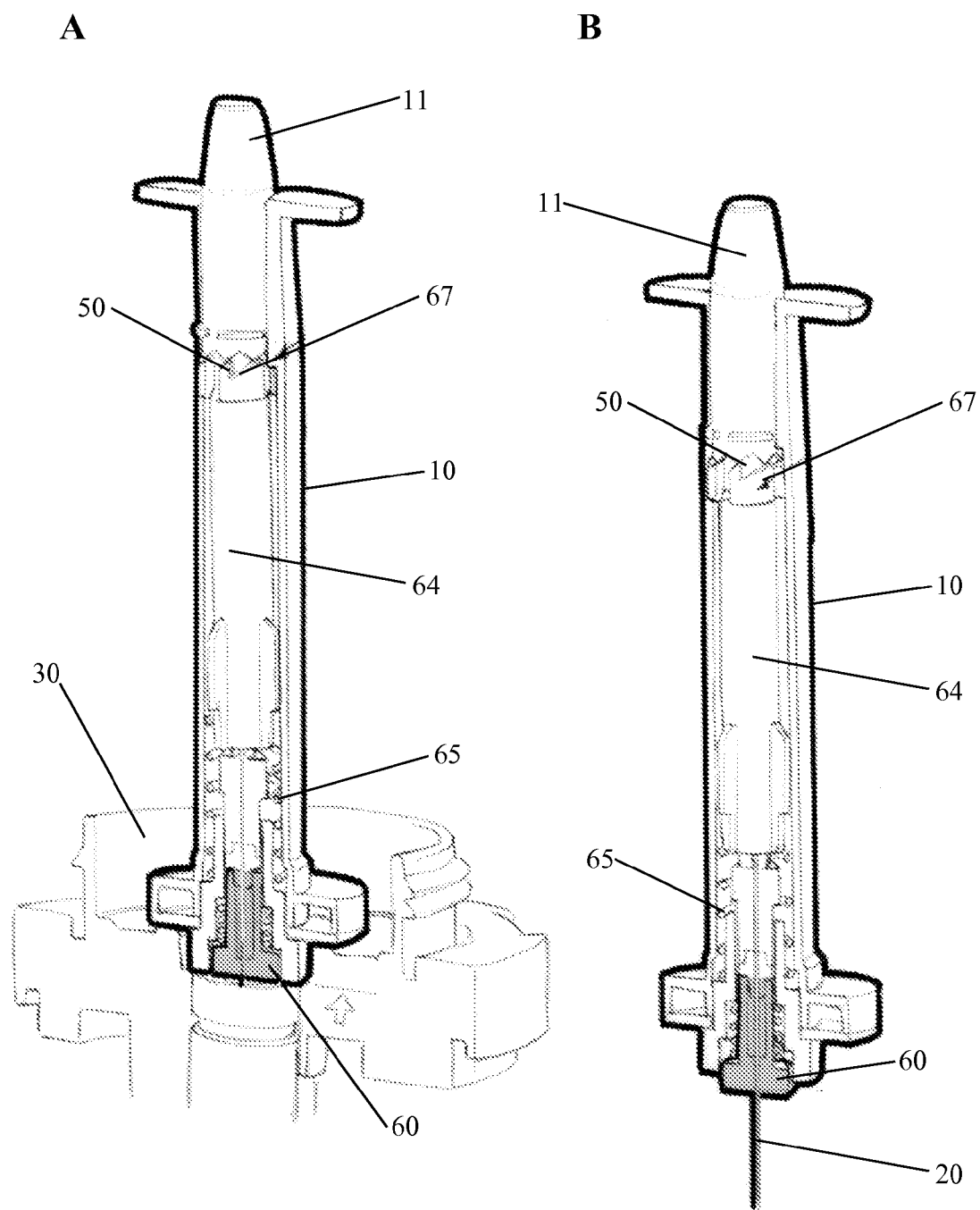
FIG. 4 is a cut-away view of an embodiment of a SPME device in which engagement with an instrument depresses the foot of the SPME to prevent the filament from being locked in an extended position; A) SPME engaged with instrument and foot depressed; B) disengaged SPME and foot extended.

FIG. 4 demonstrates an embodiment of an SPME device that comprises an extendable foot element 60 at the base of the device. The foot element 60 optionally comprises a spring 65 mechanism that causes the foot element 60 to extend beyond the bottom of the base of the SPME device, depressing the foot element 60 within the device in the presence of an external force (e.g., engagement of the device with an instrument) 30. The top portion of the foot element 60 engages an internal interference element 64 that interferes with the stepper mechanism 50 (e.g., preventing the button 11 from being fully depressed). When the SPME is disengaged from an instrument 30 (FIG. 4B), the foot element 60 sits in an extended conformation and the interference element 64 does not interfere with the stepper mechanism 50. In such a configuration, the button 11 is depressed/released to extend the filament 20 (e.g., for cleaning, for sample loading, etc.) and depressed/released to retract the filament 20 (e.g., to prepare for engagement of the SPME with the instrument). However, when the SPME engages with the instrument 30 (FIG. 3A), the foot element 60 is depressed and the interference element 64 engages (e.g., interferes) with the stepper mechanism 50. In such a configuration, depressing the button extends the filament (e.g., for sample testing, etc.), but release of the button results in the filament being withdrawn into the SPME. If the user is not actively depressing the button, the filament is withdrawn into the SPME. In such an embodiment, the button 11 is depressed for the duration of the testing. The user need only cease applying pressure to the button 11, prior to disengaging the SPME with the instrument 30, to prevent the filament 20 being in the extended conformation during the disengagement (e.g., resulting in damage to the filament).

Figure 5:
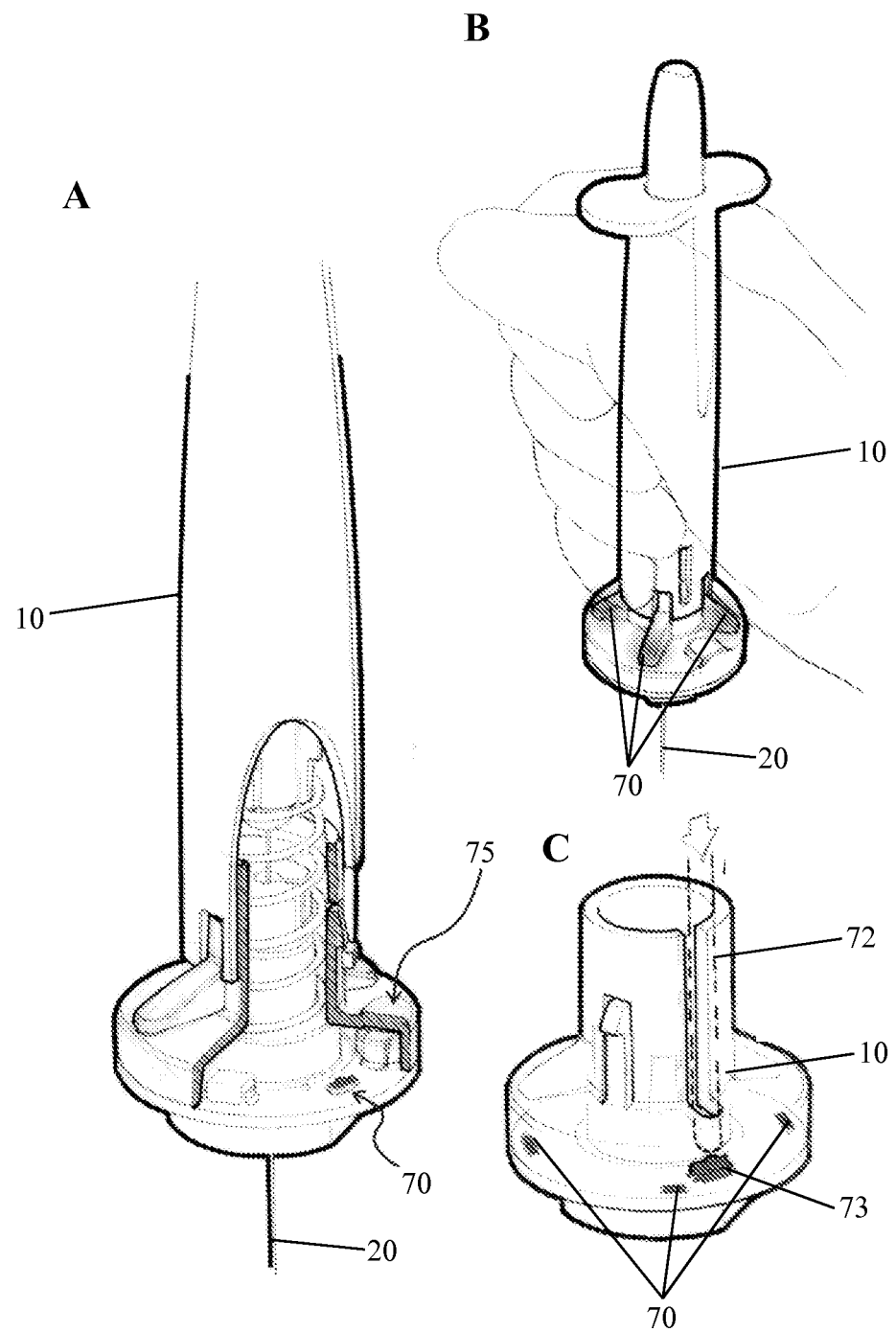
FIG. 5 shows an SPME device comprising an indicator light at the base of the housing that indicates the filament is extended; A) is cut-away view of the base of an SPME; B) is an exterior view of SPME with indicator lights; C) is view of example SPME base showing interior rib activation mechanism.

FIG. 5 demonstrates an embodiment of an SPME device that comprises an indicator light 70 (e.g., LED) or multiple indicator lights 70, at the base of the housing 10 that indicates the filament 20 is extended. Such indicator lights 70 may find use with any filament 20 extension/retraction mechanisms described herein. The extension/retraction mechanism depicted in FIG. 5 is similar to that of FIG. 2 in that a downward force (e.g., from a user's hand) extends the filament 20 from the SPME, rather than depressing/releasing a button. When the housing 10 is depressed (and the filament 20 is extended), the indicator light 70 (e.g., LED) is illuminated, indicating that the filament 20 is inserted into the instrument. The filament 20 remains in the extended configuration, and the light remains illuminated, as long as sufficient downward pressure is applied to the device housing 10. When pressure is released, the filament 20 is withdrawn into the SPME, and the indicator light 70 becomes un-illuminated. The indicator light serves to indicate to a user that the filament is inserted into the instrument, and the device should not be withdrawn without taking the necessary steps (e.g., depressing button, releasing downward pressure on housing, etc.) to properly retract the filament 20 into the SPME. Although depression of the housing 10 may result in illumination of the indicator light(s) 70 through any suitable mechanism, in some embodiments, an internal rib 72 (or other internal structure), e.g., on the interior of the housing 10, contacts a switch 75 upon depression of the housing 10, and results in illumination of the indicator light(s) 70.

Figure 6:
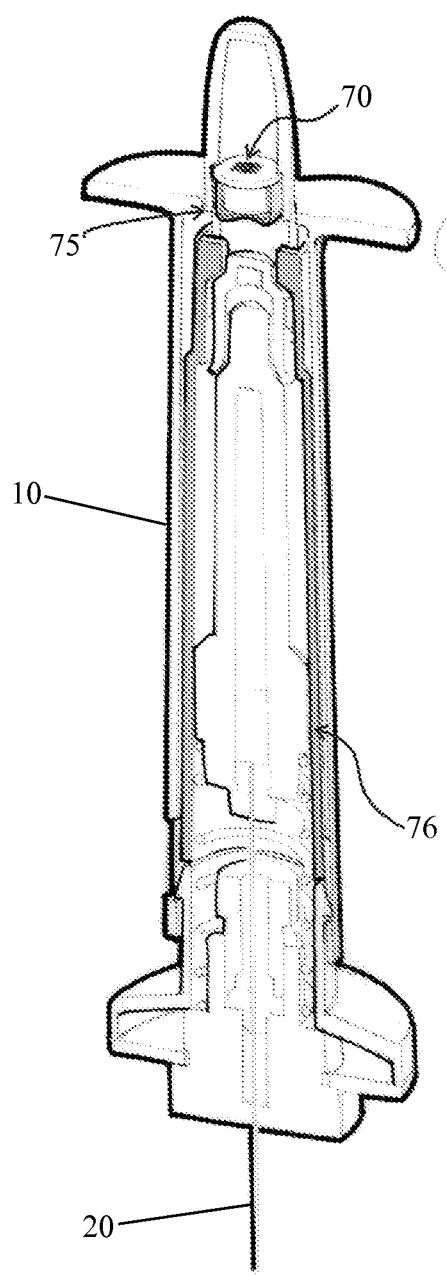
FIG. 6 shows an SPME device comprising an indicator light at the top of the housing that indicates the filament is extended; A) is a cut-away view; B) exterior view.
Figure 6:
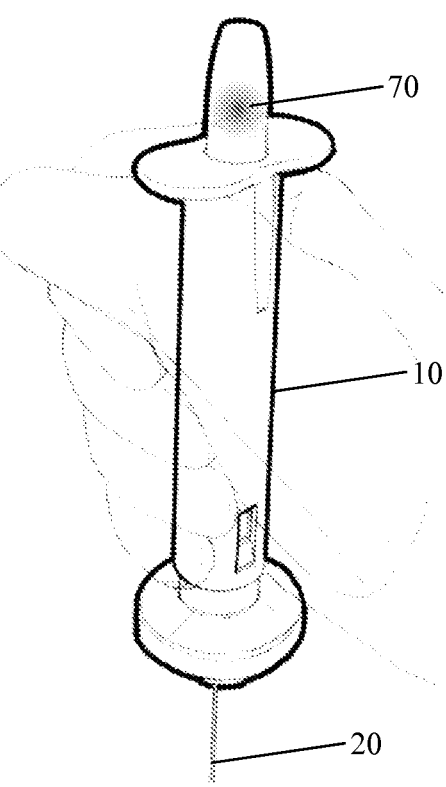

FIG. 6 demonstrates an embodiment of an SPME device that comprises one or more indicator lights 70 (e.g., LEDs) at the top of the housing 10 to indicate the filament 20 is extended. Such indicator lights 70 may find use with any filament 20 extension/retraction mechanisms described herein. The indicator light 70 at top of the SPME device functions similarly to those depicted in FIG. 5. Depression of the housing 10 results in an internal sleeve 76 interacting with the switch 75 causing illumination of the indicator light 70. In some embodiments placement of the lights at the top of the SPME device provides enhanced visibility to a user.

Figure 7:
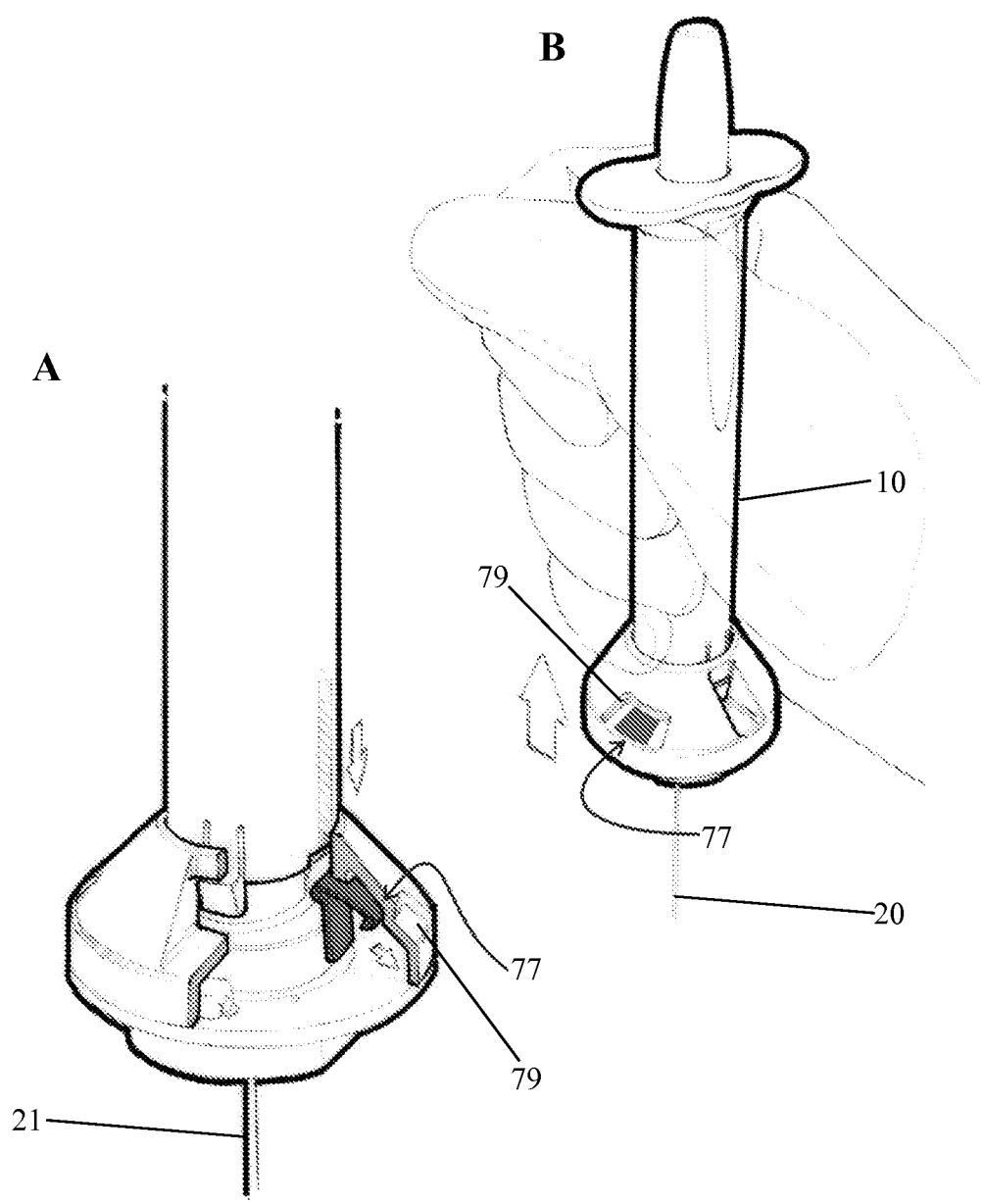
FIG. 7 shows an SPME device comprising a mechanical flag at the base of the housing that is visible when the filament is extended; A) is a cut-away view of the base; B) exterior view.

FIG. 7 demonstrates an embodiment of an SPME device that comprises a mechanical flag 77 at the base of the housing 10 that is visible when the filament 20 is extended. Such mechanical flags 77 may find use with any filament 20 extension/retraction mechanisms described herein. The mechanical flag 77 functions similarly to the indicator lights depicted in FIGS. 5 and 6, but it does not require batteries or other electrical power to operate. When the housing 10 is depressed, the mechanical flag 77 is pushed forward and becomes visible through an indicator window 79. However, it should be understood that any means of activating an indicator flag finds use in embodiments described herein.

Figure 8:
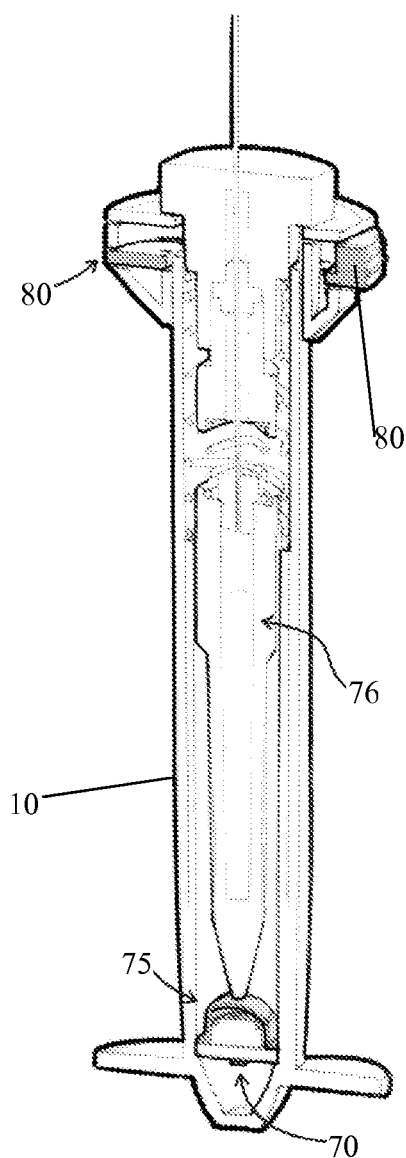
FIG. 8 shows an SPME device comprising a locking mechanism that locks the filament in the extended position when depressed, but cannot adopt the locked conformation when the SPME is engaged with an instrument; A) is a cut-away view; B) exterior view; C) is a detailed view of the locking element.
Figure 8:
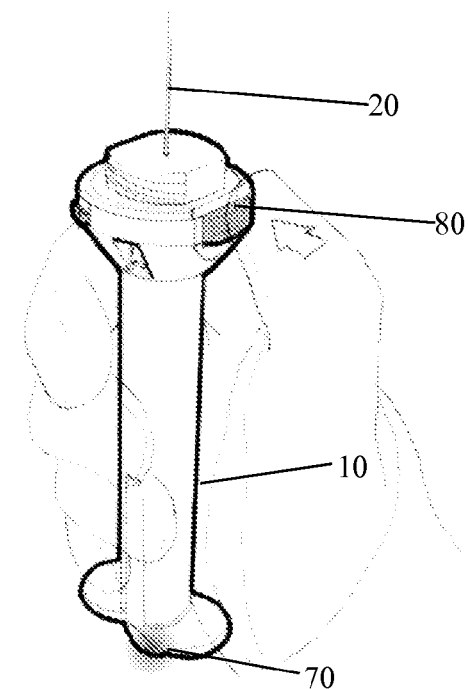
Figure 8:
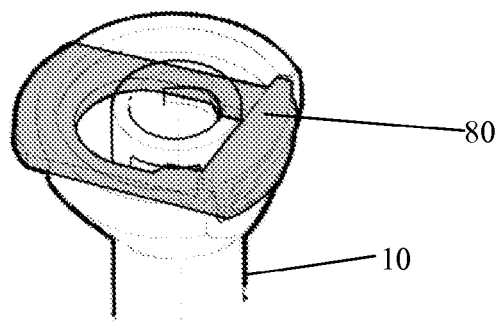

FIG. 8 demonstrates an embodiment of an SPME device that comprises a filament lock 80 at the base of the device that locks the filament 20 in the extended position when the filament lock 80 is engaged/depressed. In the embodiment depicted in FIG. 8, the filament 20 is extended from the device by placing downward pressure on the housing 10, whether or not the device is engaged with an instrument. When the pressure is released, the filament 20 withdraws into the device. However, if, while the filament 20 is extended, the filament lock 80 is engaged, the filament 20 is held in the extended conformation (e.g., for filament cleaning, for sample loading, etc.). When the filament lock 80 is disengaged, and in the absence of downward pressure on the housing 10, the filament 20 withdraws into the SPME device. To prevent the filament lock 80 from engaging while the filament 20 is inserted into an instrument, engagement of the filament lock 80 is physically incompatible with engagement of the SPME device with an instrument. A locked SPME cannot engage with an instrument and an instrument-engaged SPME device cannot become locked. Many suitable filament lock 80 configurations are compatible with embodiments of SPME devices. FIG. 8 depicts filament lock 80 that locks the filament 20 in place upon depression of a button that is part of the filament lock 80. When the filament lock 80 is depressed, the filament 20 cannot retract and the device cannot engage with an instrument. Further, the filament lock 80 cannot be depressed while engaged with the instrument. The SPME device depicted in FIG. 8 also comprises an indicator light 70 within the shaft of the device that illuminates the top of the housing when the filament 20 is extended. This indicator light serves to, for example, remind a user that the filament 20 is locked in the extended conformation before attempting to engage the device with an instrument.

Figure 9:
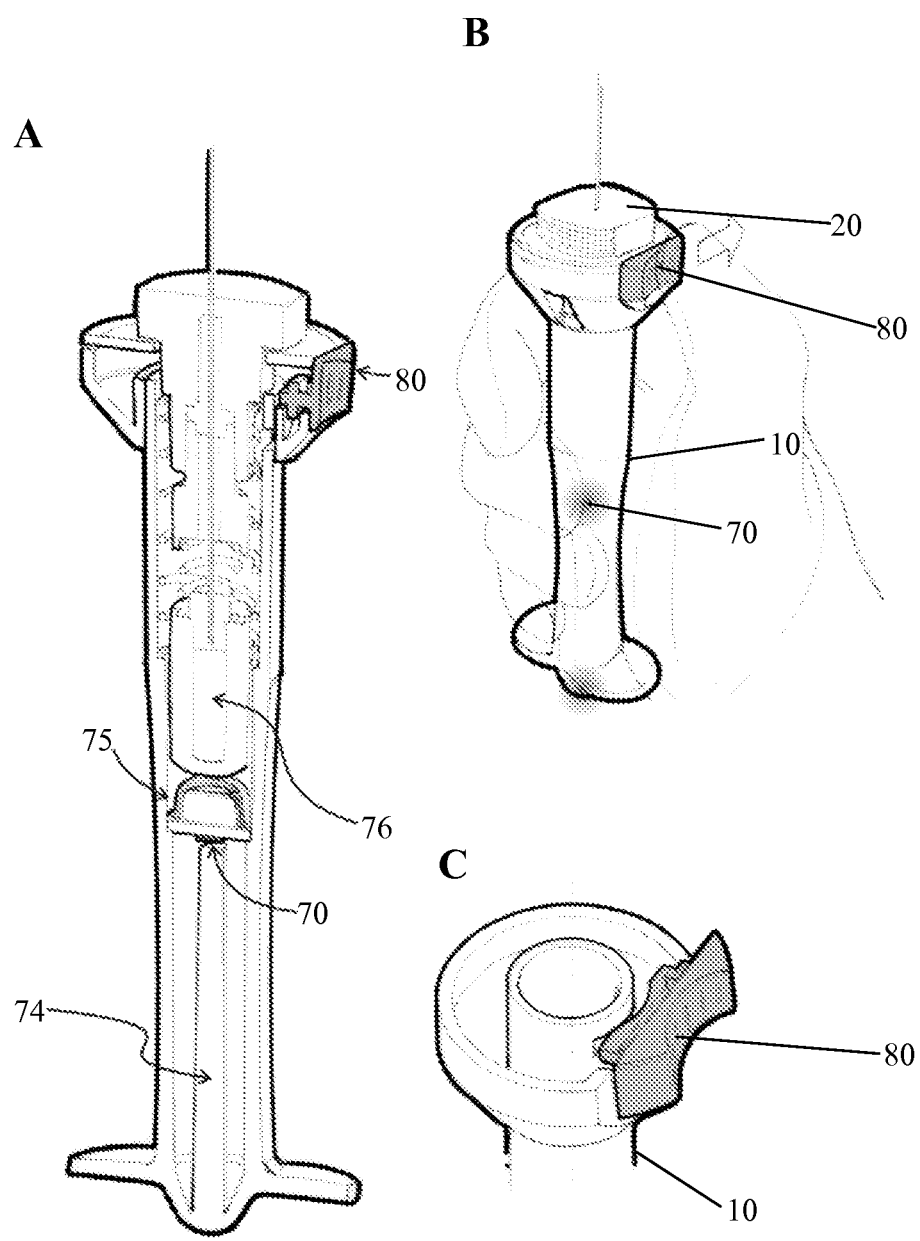
FIG. 9 shows an SPME device comprising a locking mechanism that locks the filament in the extended position when depressed, but cannot adopt the locked conformation when the SPME is engaged with an instrument; A) is a cut-away view; B) exterior view; C) is a detailed view of the locking element.

FIG. 9 demonstrates an embodiment of an SPME device that comprises a filament lock 80 that functions similarly to that depicted in FIG. 8 and described above, but is engaged through a different user action. The filament lock 80 of FIG. 9 is engaged by sliding the filament lock 80 to the side (e.g., left and/or right). When the filament lock 80 is moved into the engaged position, the filament 20 cannot retract and the device cannot engage with an instrument. Further, the filament lock 80 cannot be slid into the engaged positions while the SPME is engaged with the instrument. The SPME device depicted in FIG. 9 also comprises an indicator light 70 within the shaft of the device that illuminates the top of the housing when the filament 20 is extended. This indicator light serves to, for example, remind a user that the filament 20 is locked in the extended conformation before attempting to engage the device with an instrument.

Figure 10:
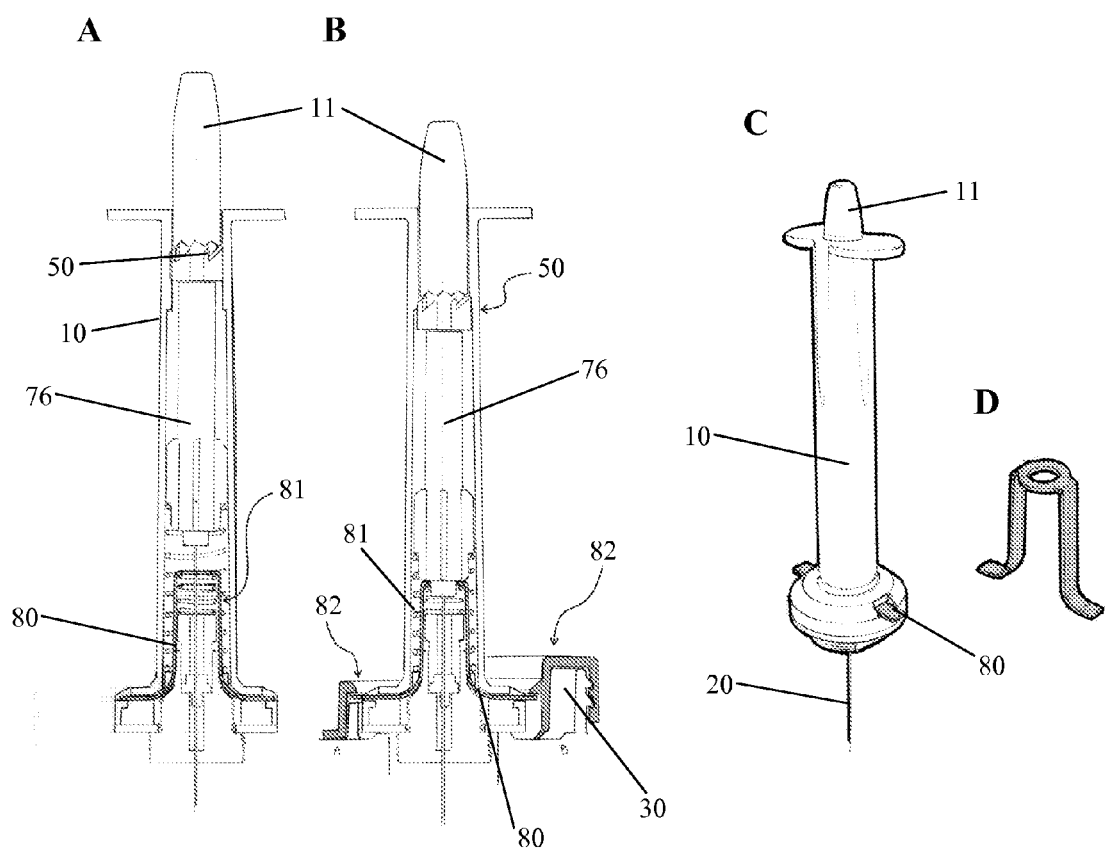
FIG. 10 shows an SPME device comprising an extended-tab locking mechanism that prevents the SPME from being withdrawn from an instrument, to which it is engaged, when the filament is in the extended position; A) is a cut-away view in which the SPME is unengaged with instrument, button raised, tabs retracted; B) is a cut-away view in which the SPME is engaged with instrument, button depressed, tabs extended; C) is an exterior view of the SPME of FIG. 10 with tabs extended; D) is a external view of the extendable tab element of FIGS. 10A-C.

FIG. 10 demonstrates an embodiment of an SPME device that comprises device lock at the base of the device. The device lock prevents the SPME device from being disengaged from an instrument 30 when the filament 20 is extended. Many suitable device locks are within the scope of embodiments provided herein. The device lock depicted in FIG. 10 comprises extendable tabs 80 that adopt an extended conformation when the filament 20 is extended from the device. When the SPME device is not engaged with an instrument 30, extension of the extendable tabs 80 has no substantial effect. However, when an SPME device is engaged with an instrument 30 (FIG. 10B) and the extendable tabs 80 adopt the extended conformation (e.g., when the filament 20 is extended from the device), extendable tabs 80 engage the instrument shoulders 82 and prevent the SPME from being withdrawn from the instrument 30. When the filament 20 is retracted into the SPME (SEE FIG. 10A), the extendable tabs 80 also retracts, thereby becoming disengaged (e.g., unlocked), and allowing the SPME to be disengaged from the instrument 30. The filament 20 of the SPME device depicted in FIG. 10 is extended and retracted by depressing/releasing a button 11 at the top of the device. The filament 20 is withdrawn in a similar fashion by depressing/releasing the same button 11. Such a mechanism does not require a user to be in contact with the SPME (or applying downward pressure) in order for the filament 20 to be extended into the instrument 30. Because the SPME device is locked to an instrument 30 to which it is engaged, when the filament 20 is extended, the device cannot be withdrawn from the instrument 30 without retracting the filament 20. Although the device lock comprising extendable tabs 80 is depicted in FIG. 10 with a particular extension/retraction mechanism (e.g., press and release button 11), such locking mechanisms may find use with any suitable extension/retraction mechanisms.

Figure 11:
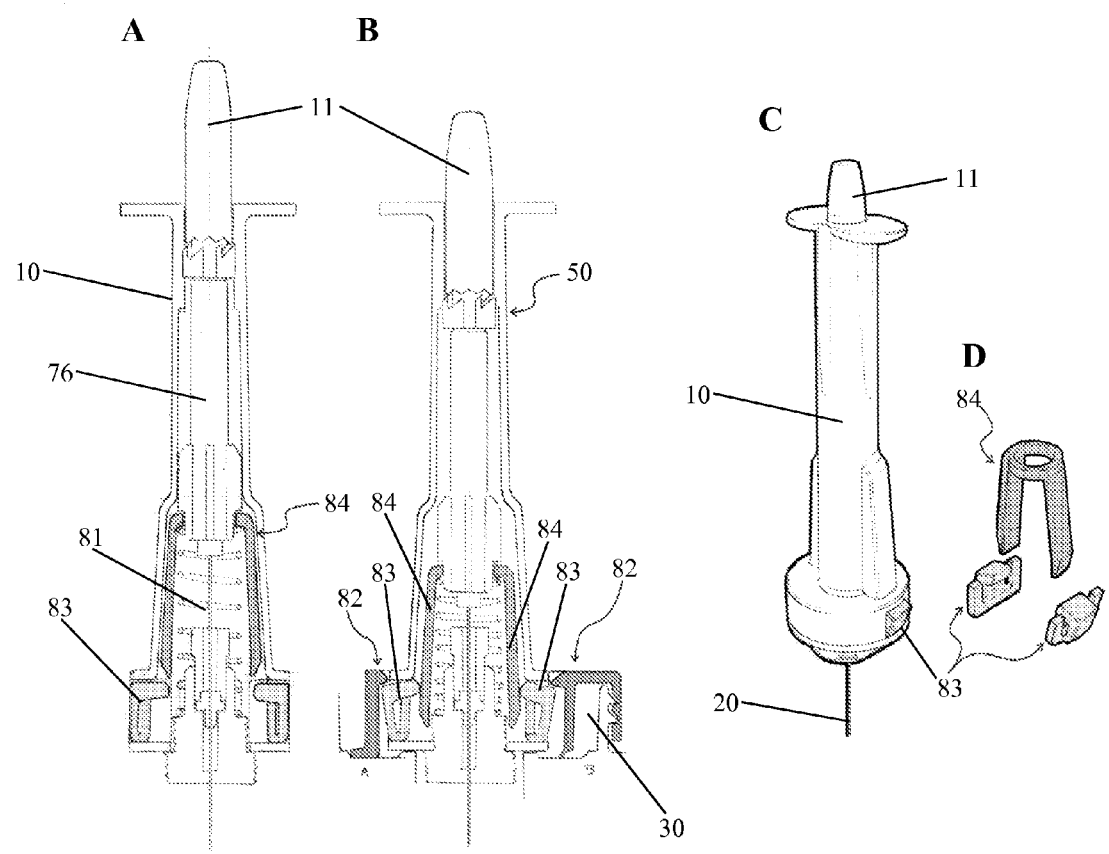
FIG. 11 shows an SPME device comprising an extended-shoulder locking mechanism that prevents the SPME from being withdrawn from an instrument, to which it is engaged, when the filament is in the extended position.

FIG. 11 demonstrates an embodiment of an SPME device that comprises a device lock at the base of the device. The device lock prevents filament breakage within an instrument by the same principle as the locking mechanism depicted in FIG. 10 and described above, but locks the SPME device to the instrument by a different means. The device lock depicted in FIG. 11 comprises a flexible-shoulder locking mechanism that prevents the SPME from being withdrawn from an instrument, to which it is engaged, when the filament is in the extended position. The device lock depicted in FIG. 11 comprises a retractable/extendable wedge 84 that adopts an extended conformation when the filament 20 is extended from the device. When extended (SEE FIG. 11B), the retractable/extendable wedge 84 contacts a flexible shoulder element 83, and the retractable/extendable wedge 84 forces the flexible shoulder element 83 outward. When the SPME device is engaged with an instrument 30, the outward extended flexible shoulder elements 83 reside beneath the collar 82 of the instrument 30, thereby preventing the SPME from being disengaged from the instrument 30. When the filament 20 is withdrawn from the instrument 30 and adopts the retracted conformation, the retractable/extendable wedge 84 adopts a retracted conformation, the flexible shoulder element(s) 83 move inward and become clear of the collar 82 of the instrument 30, thereby allowing the device to be removed from the instrument 30. The flexible shoulder elements 83 and retractable/extendable wedge 84 have no substantive effect when the device is not engaged with an instrument (SEE FIGS. 11A and C). The locking mechanism depicted in FIG. 11, and variations thereof, may find use with any suitable extension/retraction mechanisms.

Figure 12:
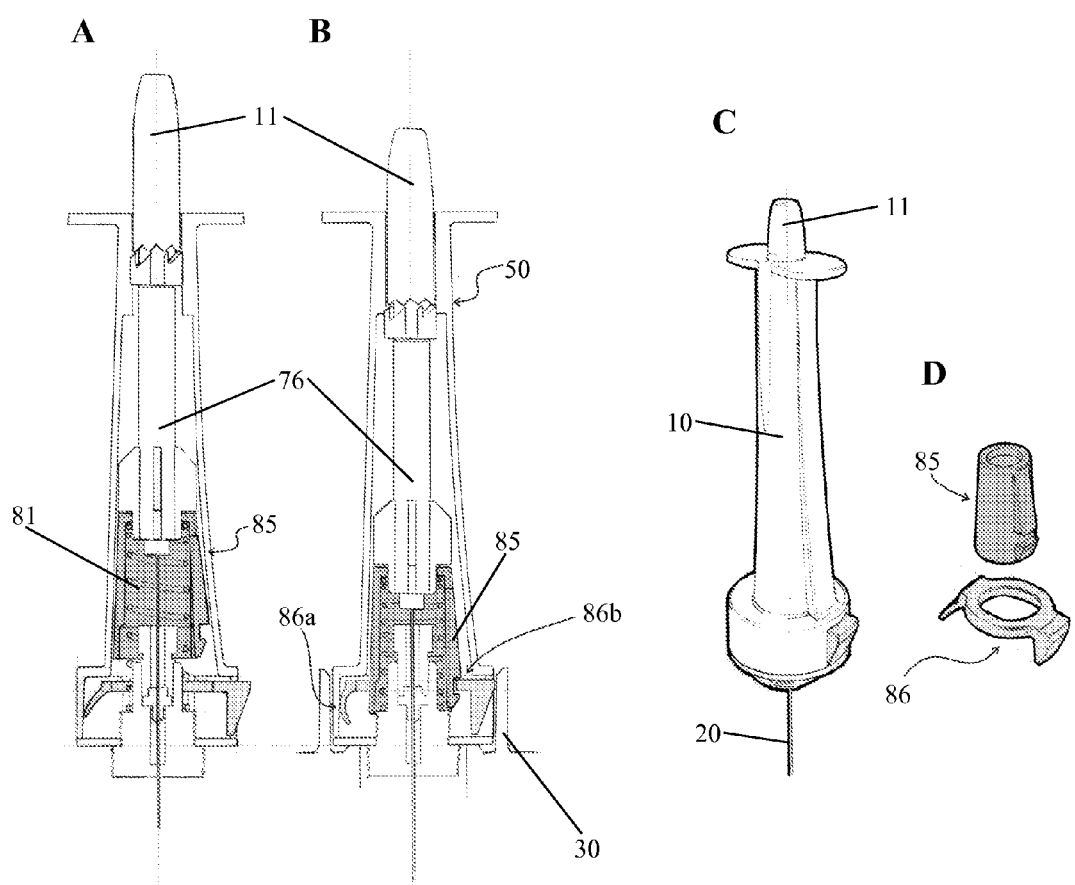
FIG. 12 shows an SPME device comprising a hook collar type mechanism that causes the filament to retract upon the SPME from being withdrawn from an instrument, to which it was engaged.

FIG. 12 demonstrates an embodiment of an SPME device that comprises locking mechanism at the base of the device. The device comprises a hook collar 85 which is attached to an internal sleeve 76 by a spring 81. The device also comprises a sliding lock 86, which comprises a flexible end 86a and an interlocking end 86b. When the SPME device is not engaged with an instrument 30, the filament 20 extends and retracts by the press and release mechanism (e.g., pen-like mechanism). The flexible end 86a of the sliding lock 86 holds the sliding lock in a position so as not to interfere with the movement of the hook collar 85 (SEE FIG. 12A). The locking mechanism has no substantive effect when the device is not engaged with an instrument. However, when the SPME device is engaged with an instrument, the interlocking end 86b contacts the instrument 30 causing the sliding lock 86 to adopt an engaged position (SEE FIG. 12B). When the button 11 is depressed with the sliding lock 86 in the engaged position, the hook collar 85 latches onto the interlocking end 86b of the sliding lock 86, thereby preventing the stepper 50 from engaging. The filament 20 is therefore held in the extended position once it is extended into an instrument 30 to which the device is engaged. When a user lifts the device to remove it from the instrument, the interlocking end 86b of the sliding lock 86 disengages with the instrument 80. The flexible end 86a of the sliding lock 86 causes the sliding lock 86 to readopt the disengaged position, releasing the hook collar 85. Without the hook collar 85 being restrained, the spring 81 causes the filament 20, internal sleeve 76, and button 11 to readopt the unengaged positions. The mechanism depicted in FIG. 12 allow the filament 20 to remain in an extended position while the device is engaged with the instrument 30, but the filament 20 automatically withdraws when the device is manually disengaged from the instrument 30.

Figure 13:
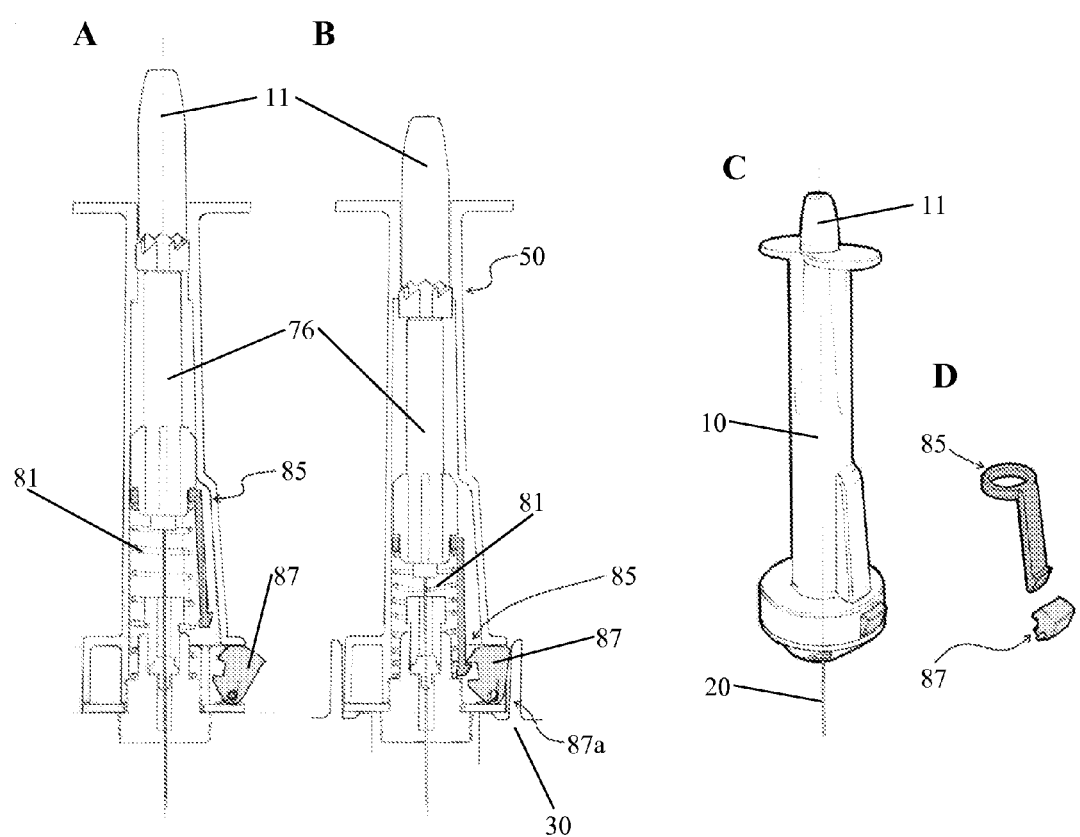
FIG. 13 shows an SPME device comprising another hook collar type mechanism that causes the filament to automatically retract upon the SPME from being withdrawn from an instrument, to which it is engaged.

FIG. 13 demonstrates an embodiment of an SPME device that comprises locking mechanism at the base of the device. The locking mechanism prevents filament breakage within an instrument by the same principle as the locking mechanism depicted in FIG. 12 and described above, but locks the SPME device to the instrument by a different means. The locking mechanism depicted in FIG. 13 comprises a pivot hook 87 locking mechanism holds the filament 20 in an extended conformation when engaged with an instrument 30, but automatically causes the filament 20 to automatically retract upon disengagement of the SPME device from the instrument 30 (SEE FIG. 13B). The locking mechanism has no substantive effect when the device is not engaged with an instrument 30 (SEE FIG. 13A). However, when the SPME device is engaged with an instrument, the pivot hook 87 adopts an engaged position (SEE FIG. 13B). When the button 11 is depressed with the pivot hook 87 in the engaged position, the hook collar 85 latches onto the pivot hook 87, thereby preventing the stepper 50 from engaging. The filament 20 is therefore held in the extended position once it is extended into an instrument 30 to which the device is engaged. When a user lifts the device to remove it from the instrument, the pivot hook 87 disengages with the instrument 80. The pivot hook 87 readopts the disengaged position, releasing the hook collar 85. Without the hook collar 85 being restrained, the spring 81 causes the filament 20, internal sleeve 76, and button 11 to readopt the unengaged positions. The mechanism depicted in FIG. 13 allows the filament 20 to remain in an extended position while the device is engaged with the instrument 30, but the filament 20 automatically withdraws when the device is manually disengaged from the instrument 30. In the embodiment depicted in FIG. 13, a torsion spring 87a causes the pivot hook 87 top adopt the disengaged conformation when not affirmatively acted upon by the instrument 30; however, other means and mechanisms for operating a locking mechanism are within the scope of embodiments, provided herein. The locking mechanism depicted in FIG. 13, and variations thereof, may find use with any suitable extension/retraction mechanisms.

Figure 14:
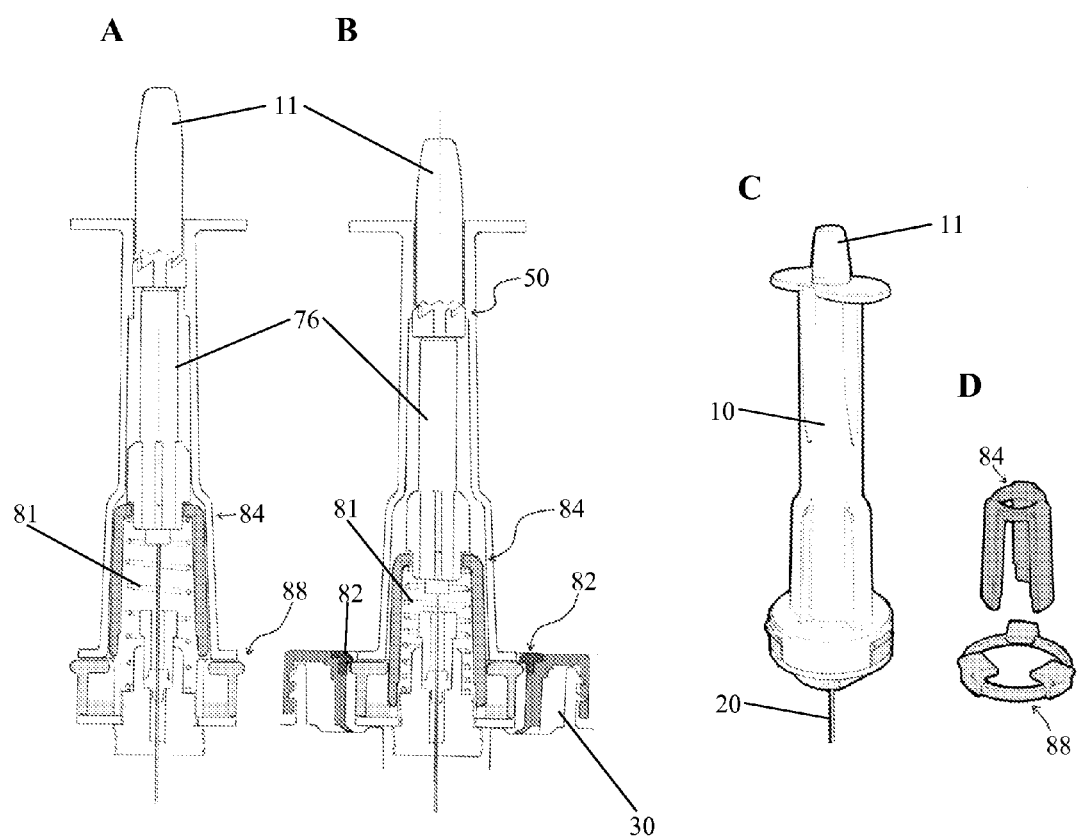
FIG. 14 shows an SPME device comprising a raised-rib locking mechanism that engages with an extended shoulder of an instrument to prevent the SPME from being withdrawn from the instrument when the filament is in the extended position.

FIG. 14 demonstrates an embodiment of an SPME device that comprises locking mechanism at the base of the device. The locking mechanism prevents filament 20 breakage within an instrument by the same principle as the locking mechanism depicted in FIGS. 10 and 11, but locks the SPME device to the instrument by a different means. The locking mechanism depicted in FIG. 14 comprises a shoulder ring 88 that engages with an extended shoulder 82 of an instrument 30. When the filament 20 is retracted the shoulder ring can move past the collar 82, to allow the device to engage and disengage with the instrument 30 (e.g., through flexing or bending of the shoulders along the shoulder ring 88). However, when the filament is extended, the retractable/extendable wedge prevents the shoulder ring 88 from adopting a conformation such that the shoulders can move past the collar 82. When the device is engaged with the instrument 30, and the filament 20 is extended, the retractable/extendable wedge 84 holds the shoulder ring 88 in a conformation that locks the SPME device to the instrument 30. When the filament 20 is withdrawn from the instrument 30 and adopts the retracted conformation, the wedge 84 is retracted, the shoulder ring 88 is allowed to adopt a disengagement conformation, the shoulder ring 88 can move past the collar 82, and the device can be removed. The locking mechanism has no substantive effect when the device is not engaged with an instrument. The locking mechanism depicted in FIG. 14, and variations thereof, may find use with any suitable extension/retraction mechanisms.

Figure 15:
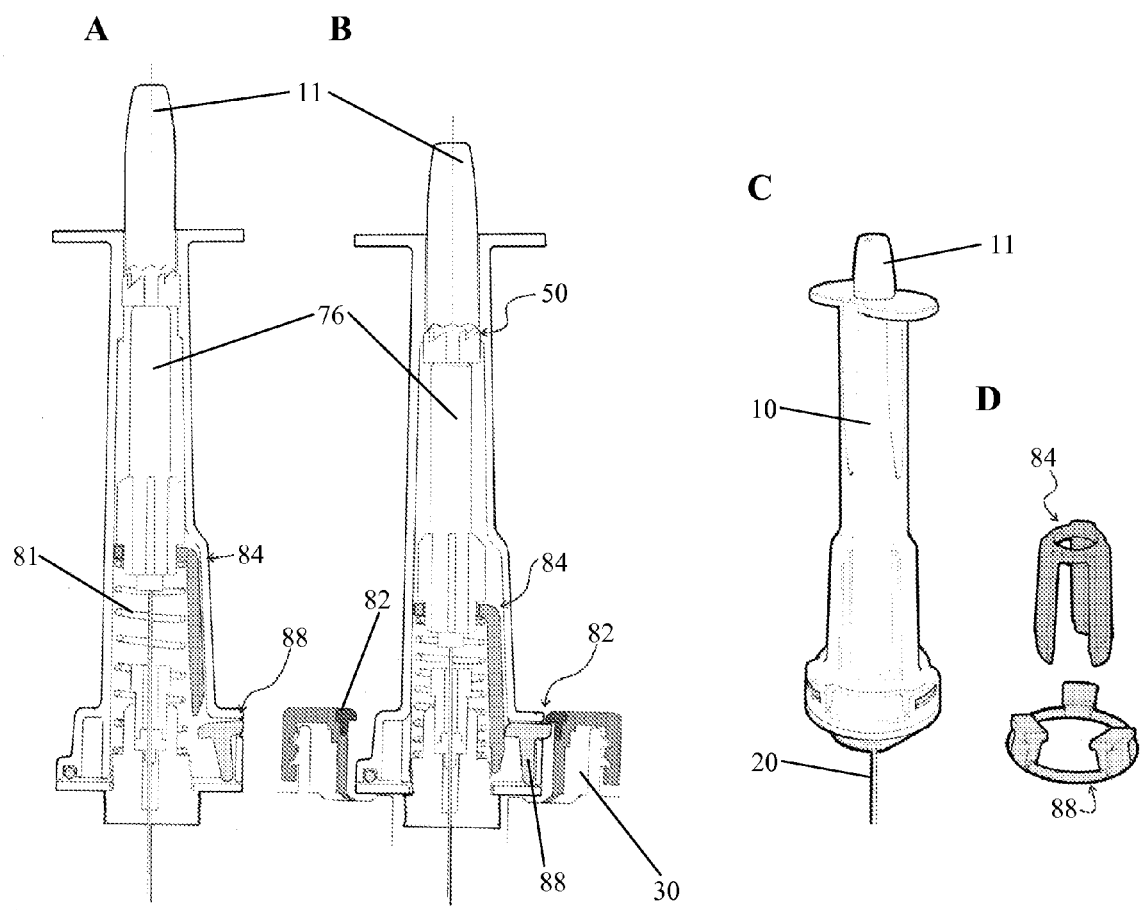
FIG. 15 shows an SPME device comprising a radial-fingers locking mechanism that engages with an extended shoulder of an instrument to prevent the SPME from being withdrawn from the instrument when the filament is in the extended position.
Figure 16:
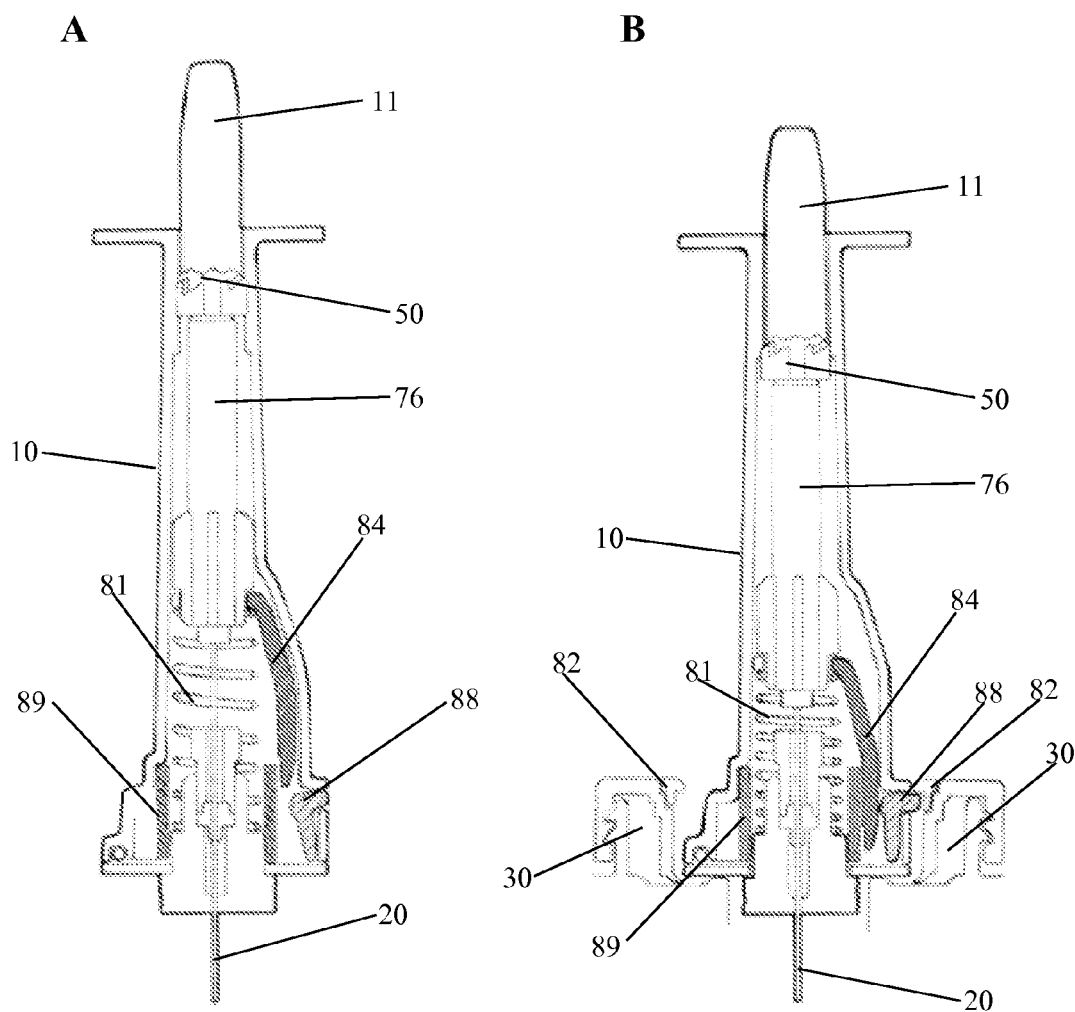
FIG. 16 shows an example locking base configuration.
Figure 17:
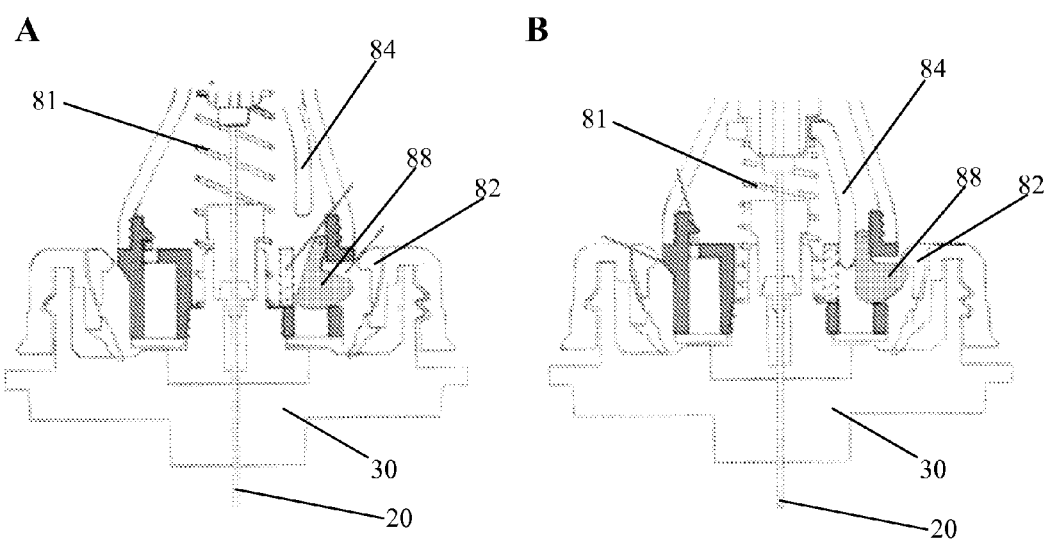
FIG. 17 shows an example locking base configuration.
Figure 18:
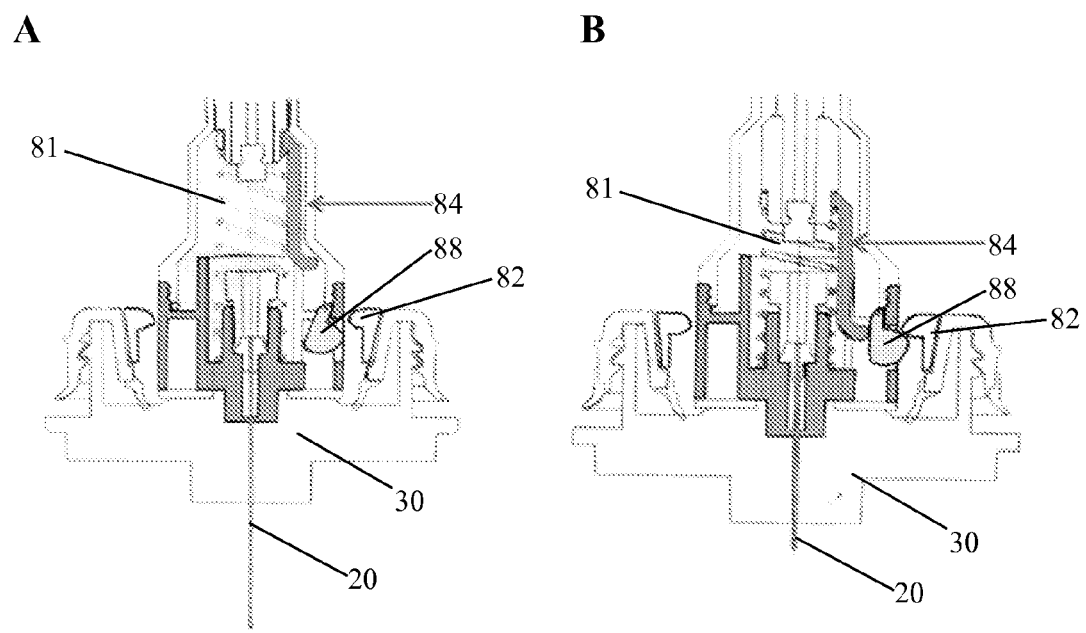
FIG. 18 shows an example locking base configuration.
Figure 19:
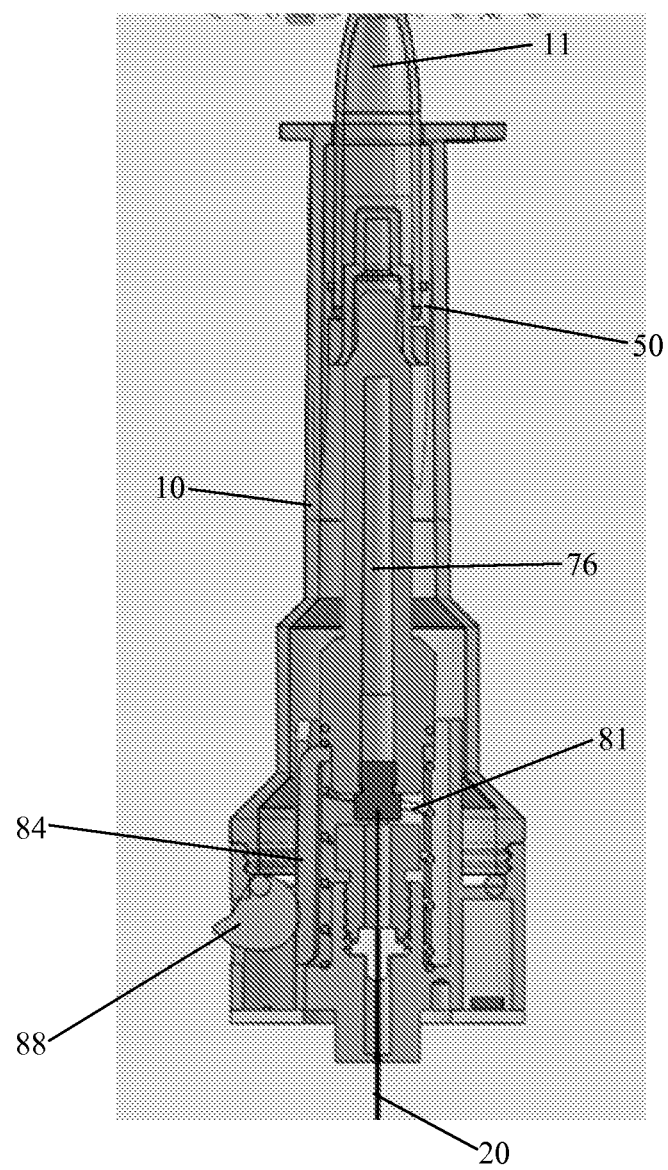
FIG. 19 shows example SPME device housing, internal workings, and locking mechanism.
Figure 20:
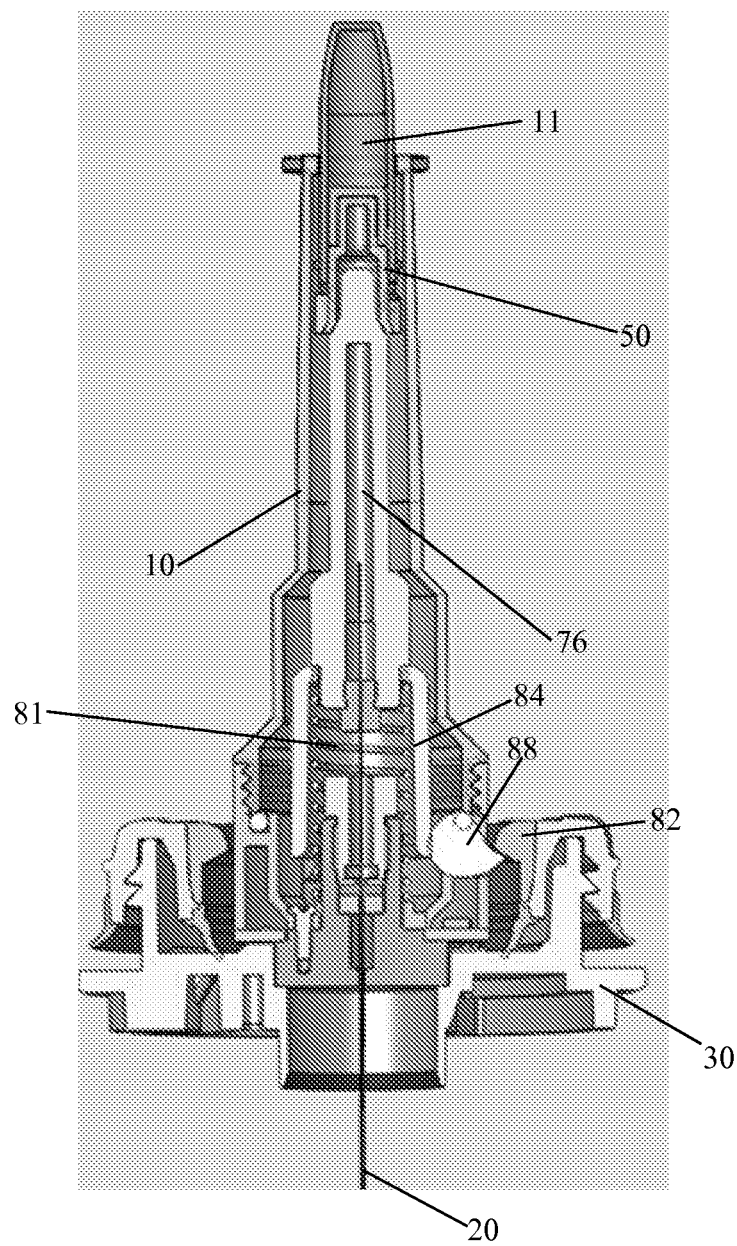
FIG. 20 shows an example SPME device engaged with an instrument.
Figure 21:
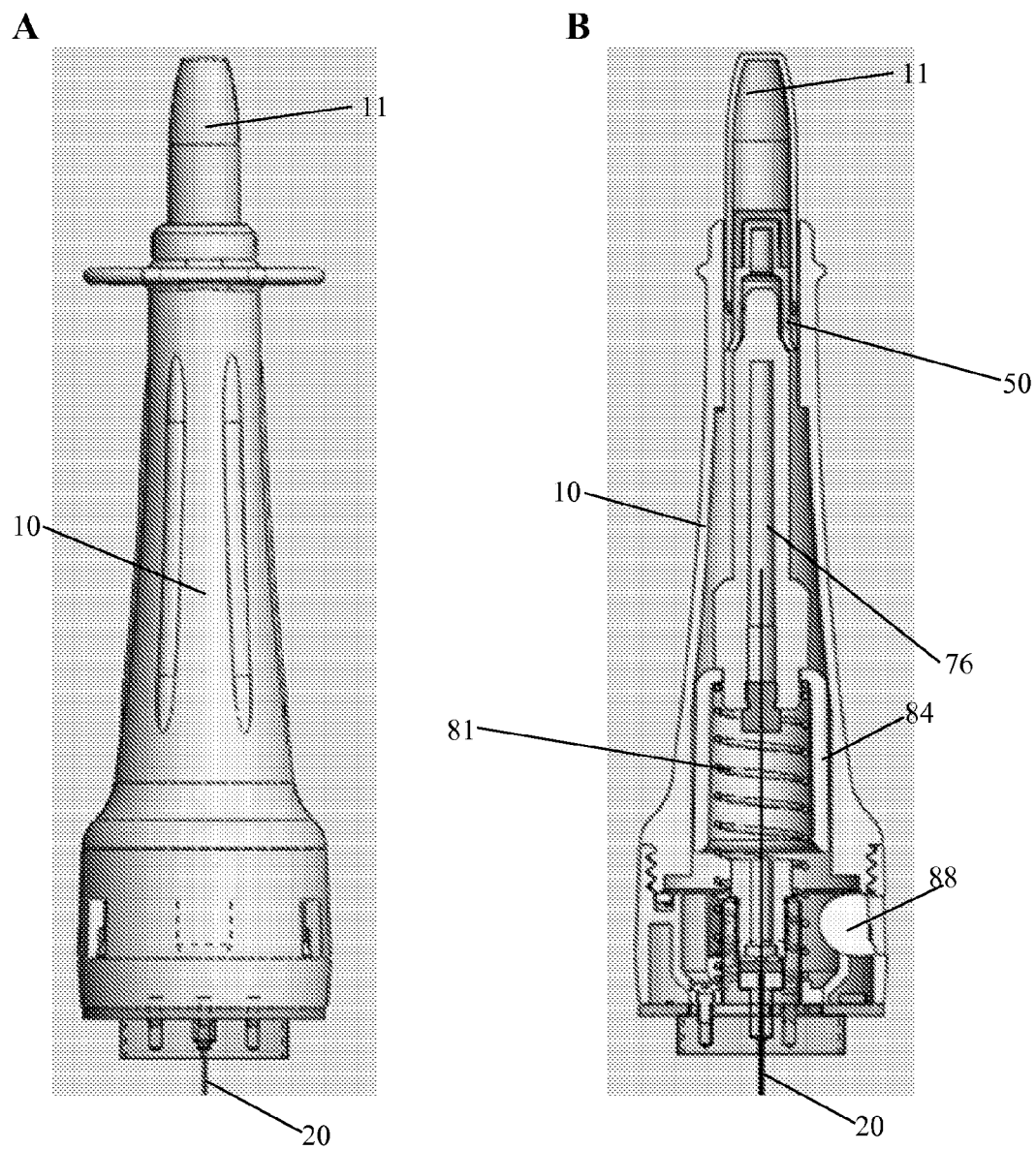
FIG. 21 shows exterior and interior views of an example SPME device.

FIG. 15 demonstrates an embodiment of an SPME device that comprises locking mechanism at the base of the device. The locking mechanism prevents filament 20 breakage within an instrument by the same principle as the locking mechanism depicted in FIG. 14 but locks the SPME device to the instrument by a different means. The locking mechanism depicted in FIG. 15 comprises a shoulder ring 88 that engages with an extended shoulder 82 of an instrument 30. When the filament 20 is retracted the shoulder ring adopts a conformation in which it is flush (or below) the outer surface of the housing, allowing it to move past the collar 82, to allow the device to engage and disengage with the instrument 30 (e.g., through flexing or bending of the shoulders along the shoulder ring 88). However, when the filament is extended, the retractable/extendable wedge drives the shoulder ring 88 outwards adopting a conformation such that the shoulders cannot move past the collar 82. When the device is engaged with the instrument 30, and the filament 20 is extended, the retractable/extendable wedge 84 holds the shoulder ring 88 in a conformation that locks the SPME device to the instrument 30. When the filament 20 is withdrawn from the instrument 30 and adopts the retracted conformation, the wedge 84 is retracted, the shoulder ring 88 is allowed to adopt a disengagement conformation, the shoulder ring 88 clears the collar 82, and the device can be removed. The locking mechanism has no substantive effect when the device is not engaged with an instrument. The locking mechanism depicted in FIG. 15, and variations thereof, may find use with any suitable extension/retraction mechanisms.

FIGS. 16-21 provide specific implementations of the embodiments, depicted in FIG. 15 and described above.

It should be understood that the embodiments depicted in FIGS. 2-21 and described above are not intended to limit the scope of the invention. Variations and combinations of the embodiments depicted in FIGS. 2-15, and described above find use in embodiments of the SPME devices described herein. It should also be understood that the specific implementations of the various embodiments described herein are intended to example implementations only. The various means and mechanisms described and depicted herein may be connected to and/or incorporated/integrated into devices in any suitable manner.

In certain embodiments, known SPME devices are modified to incorporate the locking mechanisms disclosed herein. For example, the SPME devices described in U.S. Pat. Pub. 2006/0241515 and U.S. Pat. No. 5,691,206 (both of which are herein incorporated by reference) are modified to include the locking devices and mechanisms described herein. Also, the commercial CUSTODIAN SPME syringes (from Torion Technologies), such as C-10, C-11, and C-12, may also be modified to include locking devices and mechanisms.

We claim:

1. A solid phase micro-extraction (SPME) device comprising:
   (a) a housing;
   (b) a filament;
   (c) a means for filament extension/retraction, wherein the means for filament extension/retraction extends and retracts the filament between (i) a retracted configuration in which the filament is within the housing and (ii) an extended configuration in which the filament is extended from the housing; and
   (d) a means for device locking, wherein the means for device locking prevents the SPME device from being removed from an instrument to which it is engaged while the filament is in the extended configuration, but allows the SPME device to be removed from the instrument to which it is engaged when the filament is in the retracted configuration, wherein the means for device locking is automatically activated upon extension of the filament.

2. The SPME device of claim 1, wherein the SPME device is locked to the instrument when the means for device locking is activated.

3. The SPME device of claim 1, wherein the means for device locking is automatically deactivated upon retraction of the filament.

4. The SPME device of claim 1, further comprising an indicator signal that provides a visual and/or audible cue indicating the filament is extended.

5. The SPME device of claim 1, wherein the means for device locking extends from the SPME device to engage with the instrument when the filament is extended.

6. The SPME device of claim 1, wherein the means for device locking withdraws into the SPME device to allow disengagement and/or engagement of the means for device locking with the instrument when the filament is retracted.

7. A method comprising: (a) engaging a port on an instrument with the SPME device of claim 1; (b) extending the filament into the instrument using the means for filament extension/retraction, wherein upon extension of the filament the means for device locking automatically prevents the SPME device from being disengaged from the instrument; (c) extracting the filament from the instrument using the means for filament extension/retraction, wherein upon retraction of the filament the means for device locking automatically allows the SPME device to being disengaged from the instrument; and (d) disengaging the SPME device from the port.

8. The method of claim 7, further comprising providing an audible or visual alert that the filament is extended.

* * * * *